United States Patent [19]

Hardinge

[11] 4,276,659
[45] Jul. 7, 1981

[54] MEDULLARY CANAL PLUG

[76] Inventor: Kevin Hardinge, 'Thornfield' Legh Rd., Knutsford, Cheshire WA12 8LS., England

[21] Appl. No.: 95,784

[22] Filed: Nov. 19, 1979

[30] Foreign Application Priority Data

Jun. 30, 1979 [GB] United Kingdom ............... 22808/79

[51] Int. Cl.³ ............................................... A61F 1/00
[52] U.S. Cl. ...................................... 3/1.9; 128/92 C
[58] Field of Search .................... 3/1, 1.9, 1.91–1.913; 128/92 C, 92 CA

[56] References Cited

FOREIGN PATENT DOCUMENTS 6408 1/1980 European Pat. Off. ...................... 3/1.9
2017503 10/1979 United Kingdom .......................... 3/1.9

OTHER PUBLICATIONS

"Silastic Brand Intramedullary Implant (Swanson Design)"-pamphlet by Dow Corning Corp., Medical Products Division, Midland, Mich., Jan. 1969, pp. 1–9.

Primary Examiner—Clifford D. Crowder
Attorney, Agent, or Firm—Fleit & Jacobson

[57] ABSTRACT

A medullary canal plug for use for example, when inserting the stem of a bone joint replacement into a bone canal. The plug comprising a substantially hemispherical center and a plurality of individual leaves radiating from the flat face of the center with the adjacent edges of the leaves angularly inclined relative to the faces to facilitate the partial overlapping of the leaves, when moved from a planar disposition to a frusto conical position during insertion into the bone canal.

3 Claims, 3 Drawing Figures

MEDULLARY CANAL PLUG

This invention concerns a plug for use when inserting the stem of a bone joint replacement, for example, a femoral endoprosthesis into a bone canal.

It is known to provide a plug in the medullary canal. In the past such a plug has been formed of polyethylene and has been of rigid construction, comprising a base and a cylindrical sidewall extending therefrom. The sidewall has, in one form of plug, been provided with annular ribs extending angularly downwardly from the sidewall, that is to say, towards the base of the plug. Such a plug is used, when inserted into the medullary canal, to confine the bone cement to the region of the canal in which the stem of the joint replacement is located thus to ensure efficient fixation of the joint replacement. The plug also serves, by blocking the canal to prevent blood and tissue debris moving down the canal when bone cleaning is carried out prior to insertion of the stem of the joint replacement.

One of the disadvantages of such plugs lies in the fact that, being substantially rigid they can, from time to time, become jammed in the canal before they are located in the correct position to enable the stem of the joint replacement to be fully inserted. In such cases withdrawal of the plug is often difficult and in some cases impossible and in the latter case the plug must be broken in order to enable it to be moved to allow the correct insertion of a new plug.

Another disadvantage of the known plug is that, again due to its rigidity it is essential that a range of sizes of plugs must be made.

It is therefore an object of the present invention to provide a plug which does not suffer from the above outlined disadvantages.

Thus according to the present invention a medullary canal plug is characterized in that it comprises a relatively rigid center and a plurality of individual leaves radiating therefrom, the said leaves being so connected to the center that they can pivot from a substantially flat disc configuration to a condition in which they take up a frusto conical configuration in which the individual leaves lie in partially overlapping condition.

The invention will now be described further, by way of example only, with reference to the accompanying diagrammatic illustrations in which.

As can be seen the plug comprises a center 10 which is conveniently hemi-spherical in form.

Figure 1:
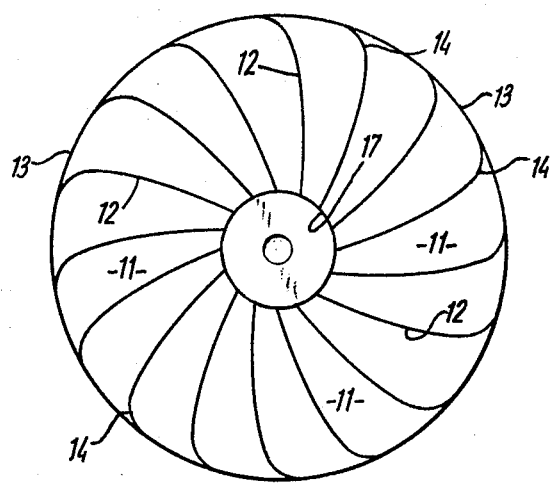
FIG. 1 is a plan view of a plug.
Figure 2:
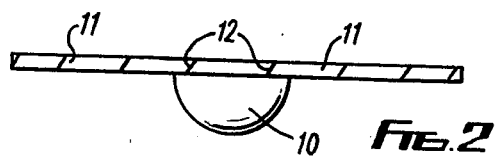
FIG. 2 is a side elevation of the plug of FIG. 1.

From the planar face of the center 10 radiate a plurality of leaves 11 which, when the plug is not in use, lie in a common plane. It will be noted that the longitudinal edges 12 of the leaves 11 are inclined (see FIG. 2 in particular) relative to the faces of the leaves and that in the region of the periphery 13 of the leaves the longitudinal edges 12 are angularly contoured (as shown at 14) relative to the edges 12 so that, as will be explained below, the leaves 11 can be caused to overlap.

Figure 3:
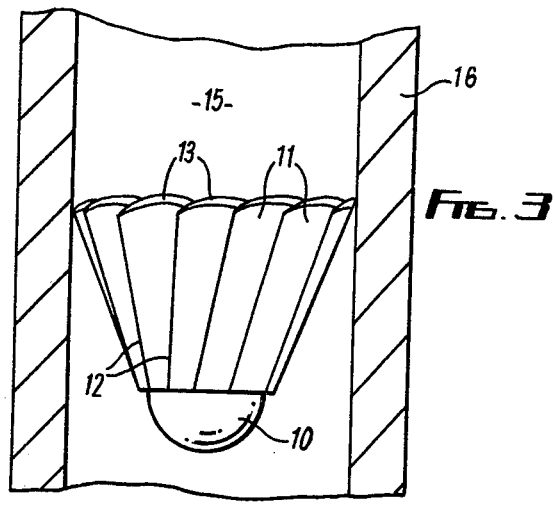
FIG. 3 shows the plug of FIGS. 1 and 2 in position in the medullary canal of a bone.

When the plug is being used it is placed over the end of the medullary canal 15 of a bone 16 and is pushed down the canal 15 by applying pressure to the center 10. Pressure on the center 10 by an inserting tool (not shown) causes the leaves 11 to pivot about a joint line 17 with the center 10 and take up a frusto conical configuration in which the leaves 11 overlap as shown in FIG. 3. Overlapping of the leaves 11 is assisted and ensured by virtue of the angular disposition, relative to the faces, of the longitudinal edges 12 of the leaves 11 and also by the contouring of the peripheral region 14 of the ends of the leaves. Since the plug leaves 11 are capable of independent movement relative to each other irregularity or change in the size of the medullary canal 15 can be compensated for by such relative movement of the leaves 11 and thus the plug can be moved to its requisite position in the canal 15 relatively easily.

It is envisaged that the plug will be moulded from rigid polyethylene and that for all uses a single size of plug can be produced, and that an X-Ray telltale will be incorporated into the plug.

I claim:

1. A medullary canal plug comprises a relatively rigid center and a plurality of individual leaves radiating therefrom, the said leaves being so connected to the center that they can pivot from a substantially flat disc configuration to a condition in which they take up a frusto conical configuration in which the individual leaves lie in partially overlapping condition.

2. A medullary canal plug as set forth in claim 1, in which the individual leaves have their adjacent edges inclined relative to the plane of their faces to facilitate the leaves, when pivoted from the flat disc configuration, to take up the partially overlapping relationship.

3. A medullary canal plug as set forth in claim 1, in which the relatively rigid center is substantially hemispherical, the leaves radiating from the flat face of the hemisphere.

* * * * *